US012279857B2

(12) United States Patent
Wolfe et al.

(10) Patent No.: US 12,279,857 B2
(45) Date of Patent: Apr. 22, 2025

(54) VIDEO USED TO ESTIMATE VITAL SIGNS

(71) Applicant: Hill-Rom Services, Inc., Batesville, IN (US)

(72) Inventors: Gene J. Wolfe, Pittsford, NY (US); Eric Dustin Agdeppa, Cary, NC (US); Tyler Holmes, Monroe, CT (US); Ibne Soreefan, West Chester, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 528 days.

(21) Appl. No.: 17/657,502

(22) Filed: Mar. 31, 2022

(65) Prior Publication Data

US 2022/0313112 A1 Oct. 6, 2022

Related U.S. Application Data

(60) Provisional application No. 63/169,734, filed on Apr. 1, 2021.

(51) Int. Cl.
*A61B 5/08* (2006.01)
*A61B 5/00* (2006.01)
*G06T 7/00* (2017.01)

(52) U.S. Cl.
CPC .......... *A61B 5/0816* (2013.01); *A61B 5/0077* (2013.01); *A61B 5/4806* (2013.01); *G06T 7/0012* (2013.01); *A61B 2576/00* (2013.01)

(58) Field of Classification Search
CPC ... A61B 5/0816; A61B 5/0077; A61B 5/4806; A61B 2576/00; A61B 5/6889;
(Continued)

(56) References Cited

U.S. PATENT DOCUMENTS 8,790,269 B2  7/2014  Xu et al.
8,977,347 B2  3/2015  Mestha et al.
(Continued)

FOREIGN PATENT DOCUMENTS

CN    111832464 A    10/2020
WO    2016/116307 A1    7/2016
(Continued)

OTHER PUBLICATIONS

Chen et al., "Collaborative use of RGB and thermal imaging for remote breathing rate measurement under realistic conditions," Infrared Physics & Technology, vol. 111, https://doi.org/10.1016/j.infrared.2020.103504, 3 pages (Abstract) (Dec. 2020).
(Continued)

*Primary Examiner* — Santiago Garcia
(74) *Attorney, Agent, or Firm* — Merchant & Gould P.C.

(57) ABSTRACT

Monitoring patient vital signs is performed by analyzing videos recorded of a patient. An algorithm is used to compute the real-time patient vital signs based on video images of the patient. These images can be captured by a video monitoring device positioned over a patient's bed. The video monitoring device can include a thermal camera and a near infrared camera that continuously send video images to a processing unit. The thermal image is used to locate the patient's face and chest. The images are analyzed with an algorithm employed to determine a patient's heart rate, respiration rate, temperature, and body position.

19 Claims, 14 Drawing Sheets

(58) Field of Classification Search
CPC ....... A61B 5/0046; A61B 5/0013; A61B 5/01; A61B 5/02055; A61B 5/02433; A61B 5/113; A61B 5/4887; A61B 5/7257; G06T 7/0012; G06T 2207/10016; G06T 2207/10048; G06T 2207/20056; G06T 2207/30201; G06T 7/0016

See application file for complete search history.

(56) References Cited

U.S. PATENT DOCUMENTS

| | | | |
|---|---|---|---|
| 9,245,196 | B2 | 1/2016 | Marks et al. |
| 9,301,710 | B2 | 4/2016 | Mestha et al. |
| 9,320,440 | B2 | 4/2016 | Kyal et al. |
| 9,674,458 | B2 | 6/2017 | Teich et al. |
| 10,143,377 | B2 | 12/2018 | Tsien et al. |
| 10,178,958 | B2 | 1/2019 | Kaestle et al. |
| 10,349,894 | B2 | 7/2019 | Shan |
| 10,524,725 | B2 | 1/2020 | Jeanne |
| 2016/0206216 | A1* | 7/2016 | Kirenko ............. A61B 5/02055 |
| 2017/0238805 | A1* | 8/2017 | Addison .............. A61B 5/7221 |
| 2019/0313914 | A1 | 10/2019 | Kirenko et al. |
| 2019/0350471 | A1 | 11/2019 | Marks et al. |
| 2020/0013147 | A1* | 1/2020 | Miyajima ................. G06T 7/70 |
| 2020/0155040 | A1 | 5/2020 | Soreefan et al. |
| 2021/0315467 | A1* | 10/2021 | Winter .................. A61B 5/024 |

FOREIGN PATENT DOCUMENTS

| | | |
|---|---|---|
| WO | 2017/120384 A1 | 7/2017 |
| WO | 2019/196131 A1 | 10/2019 |

OTHER PUBLICATIONS

Hu et al., "Combination of Near-Infrared and Thermal Imaging Techniques for the Remote and Simultaneous Measurements of Breathing and Heart Rates Under Sleep Situation," PLoS One 13(1):e0190466. https://doi.org/10.1371/journal.pone.0190466, 14 pages (Jan. 5, 2018).

* cited by examiner

VIDEO USED TO ESTIMATE VITAL SIGNS

RELATED APPLICATION(S)

This patent application claims the benefit of U.S. Patent Application No. 63/169,734 filed on Apr. 1, 2021, the entirety of which is hereby incorporated by reference.

BACKGROUND

Caregivers often check vital sign measurements of a patient under their care at regular intervals to monitor the status of the patient. One vital sign that is monitored is respiration rate. Respiration rate is the number of breaths a person takes per minute. The rate is usually measured when a person is at rest and involves counting the number of breaths per minute. In addition, the quality and depth of respiration, such as shallow breathing or labored breathing, and the uniformity of breath may be monitored.

Measuring the respiration rate of a patient can be difficult because respiration rate is often still measured manually (e.g., by a caregiver counting how many times the chest of the patient moves up and down while breathing for a period of time). Additionally, respiration rate is slower compared to other vital signs (e.g., a normal respiration rate for an adult at rest is 12 to 20 breaths per minute) and can be difficult and cumbersome to measure manually. For that reason, the respiration rate may be imprecisely estimated based on a quick visual assessment of the patient.

SUMMARY

In general terms, the present disclosure relates to the analysis of video that is used to calculate vital signs of the patient, including one or more of respiration rate, body temperature, and heart rate. In some embodiments, the video analysis can be used to determine a body position and/or estimate a pose of the patient.

The details of one or more techniques are set forth in the accompanying drawings and the description below. Other features, objects, and advantages of these techniques will be apparent from the description, drawings, and claims.

DETAILED DESCRIPTION

Figure 1:
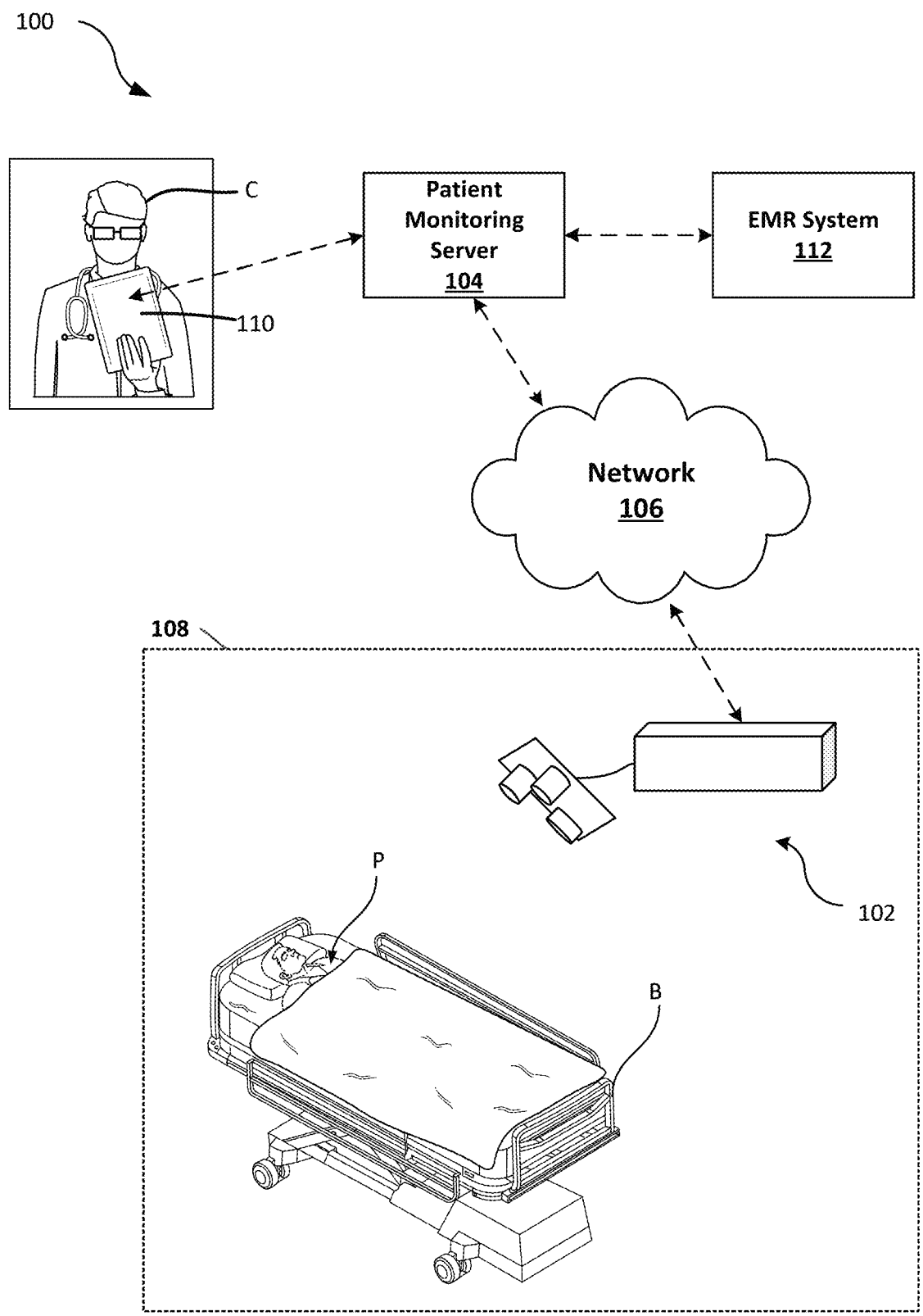
FIG. 1 is a schematic diagram illustrating a patient monitoring system.

The present disclosure is directed to monitoring patient vital signs using a video monitoring device. In the examples provided herein, the video monitoring device can include a multidimensional sensor system. Example sensors can be passive (e.g., measuring energy emission from a field of view) and/or active (e.g., emitting energy and capturing characteristics of a returned signal).

The video monitoring device enables contactless patient monitoring around the clock. This contributes significantly to patient's safety and comfort and assists with clinical workflow. An algorithm is used to compute the real-time patient vital signs based on video images of the patient captured by the video monitoring device. The video monitoring device and accompanying algorithm can be employed to monitor patient heart rate, respiration rate, temperature, and body position.

In some examples, the video monitoring device (described further below in FIGS. 1-2) is composed of a thermal camera and a near infrared (NIR) camera that continuously send video images to the processing unit at a specific frame rate (E.g., 10 fps, 30 fps, 60 fps, etc.). In some examples, the frame rate is computed as a function of the observable feature being measured. For instance, the frame rate can be set to be at least double that of the determined vital sign and/or movement within the field of view.

The video monitoring device contains NIR LEDs that continuously illuminate the scene at adequate intensity to obtain good image signals. The video monitoring device leverages the thermal image to locate the center (e.g., center of mass) of the patient's face in the thermal image. The face center is then mapped onto the NIR image as a point of reference.

The system draws a green rectangle (region of interest) on the NIR image to define the face region. The region of interest can take any form, such as the rectangular bounding box or another polygonal shape. The system then draws two blue rectangles (Right & Left regions of interest) below the face region to define two chest regions to monitor for small respiration movements. In some embodiments, the video monitoring device can include additional cameras and other features to capture other types of images of the patient.

For instance, in alternative embodiments, other devices having passive and/or active sensors can also be used to measure observable aspects in the field of view. For instance, in another embodiment, depth and/or a spatial arrangement of objects in a field of view can be measured using cameras including, without limitation, light detection and ranging (Lidar), millimeter wave (mmWave) radar, or other radiofrequency (RF) sensors.

The pixels forming the rectangular regions of interest (ROIs) are used in the respiration rate computation. The system computes, separately, the average pixel value over each rectangular chest region for each video frame. The layout of the two chest regions ensures at least one of the two rectangles overlaps with the patient's body pixels in the video image. Examples of the digital average chest pixel signal computed by the processing unit is shown on FIG. 8.

Figure 3:
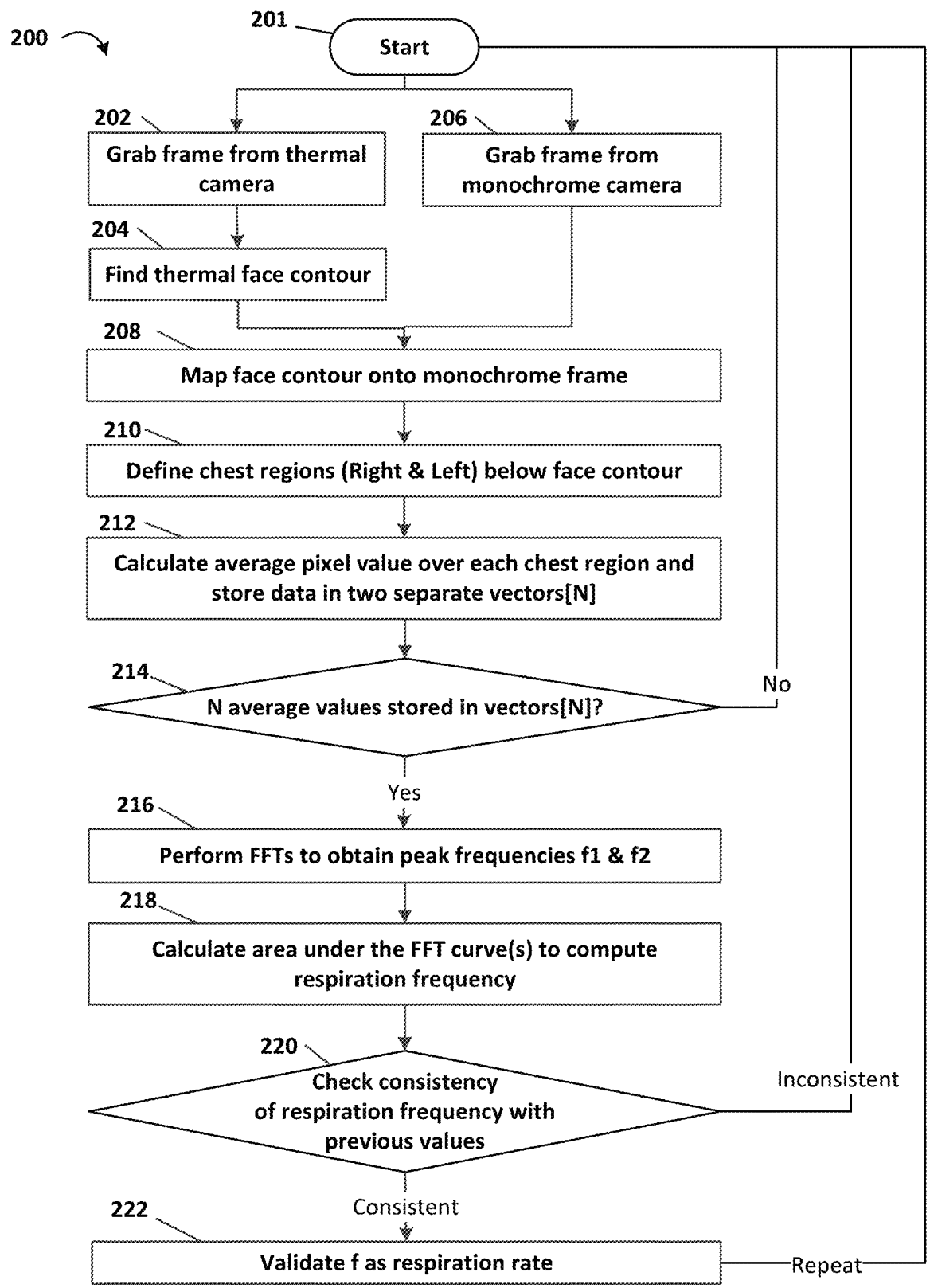
FIG. 3 is a flow chart of an example method of monitoring a patient's respiration rate.
Figure 4:
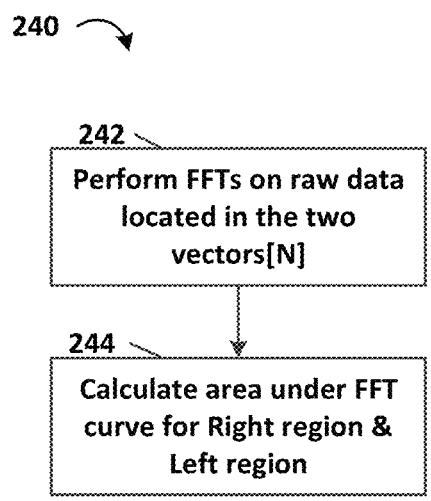
FIG. 4 is a flow chart of one possible method for performing fast Fourier transforms on data received from the video monitoring device of FIG. 1.

The computation process of the respiration rate is described in the flow chart presented in FIGS. 3-4.

The examples described herein can be employed to monitor multiple different physical parameters of a patient. These include facial temperature, heart rate, and respiration rate. Additionally, a patient's body position on a bed can be determined. The body position can be used for early warning detection of a bed exit.

As used herein, the terms "concurrently" and "contemporaneously" connote operations that occur precisely simultaneously (e.g. at the exact same time) as well as operations that occur approximately simultaneously (e.g. having a delay or lag between actions of up to several seconds).

As used herein, the term "grab" as used in reference to an image frame, describes the process of taking one still image from a video. This could happen as the video is being recorded and the still image is taken in real time. This could also happen with a video that was previously recorded.

FIG. 1 is a schematic diagram illustrating a patient monitoring system 100. The system 100 can be implemented, for example, at a hospital, clinic, or other healthcare facility. In the example of FIG. 1, the patient monitoring system 100 includes a patient location 108 with a patient bed B configured to support a patient P. In some embodiments, the bed B could be a different type of patient support device such as a lift, chair, stretcher, reclining chair, adjustable bed, or table. While the present disclosure is not limited to any particular patient support apparatus, a bed will be used as an example throughout for convenience. In some embodiments, the patient bed B is a smart bed equipped with a memory device and a processing device. The smart bed can include various functionalities to monitor a patient, entertain a patient, and make a patient more comfortable. One such example of a smart bed is the Centrella® Smart+Bed manufactured by Hill-Rom® of Batesville, Indiana.

A video monitoring device 102 is positioned in the patient location 108 above the patient bed B such that the patient P is within the field of view of cameras included in the video monitoring device 102. In some embodiments, the video monitoring device 102 is positioned approximately 7 to 8 feet away from the patient. The video monitoring device 102 is in communication with a patient monitoring server 104 through a network 106. The video monitoring device 102 is described in greater detail with reference to FIG. 2.

Vital sign data received from the video monitoring device 102 is processed at the patient monitoring server 104. The patient monitoring server 104 communicates with other computing systems such as a computing device 110 operated by a caregiver C and an electronic medical record (EMR) system 112. The caregiver C can receive updates directly from the patient monitoring server 104 or through intermediate communications with other computing systems such as a caregiver call system. Vital sign data that has been processed by the patient monitoring server 104 can be displayed on a graphical user interface (GUI) of the caregiver's computing device 110. Vital sign data processed by the patient monitoring server 104 can also be communicated to the EMR system 112 to be recorded with a medical record associated with the patient P.

In some embodiments, the patient monitoring server 104 is an independent computing system such as a remote server accessible via the network 106. In some embodiments, the patient monitoring server 104 is incorporated with the video monitoring device 102. In some embodiments, the patient monitoring server 104 includes a processor and memory device. The memory device can include instructions for the processor to analyze data received from patient monitoring devices. In some embodiments, the patient monitoring server 104 is configured to process multiple types of patient vital sign data from multiple different devices. In some embodiments, there is no patient monitoring server 104 and the video monitoring device 102 communicates directly with the caregiver's computing device 110.

The network 106 operates to mediate communication of data between network-enabled computing systems. In various embodiments, the network 106 includes various types of communication links. For example, the network 106 can include wired and/or wireless links, including cellular, Bluetooth, ultra-wideband (UWB), 802.11, ZigBee, and other types of wireless links. The network 106 can include one or more routers, switches, mobile access points, bridges, hubs, intrusion detection devices, storage devices, standalone server devices, blade server devices, sensors, desktop computers, firewall devices, laptop computers, handheld computers, mobile telephones, vehicular computing devices, and other types of computing devices.

Figure 2:
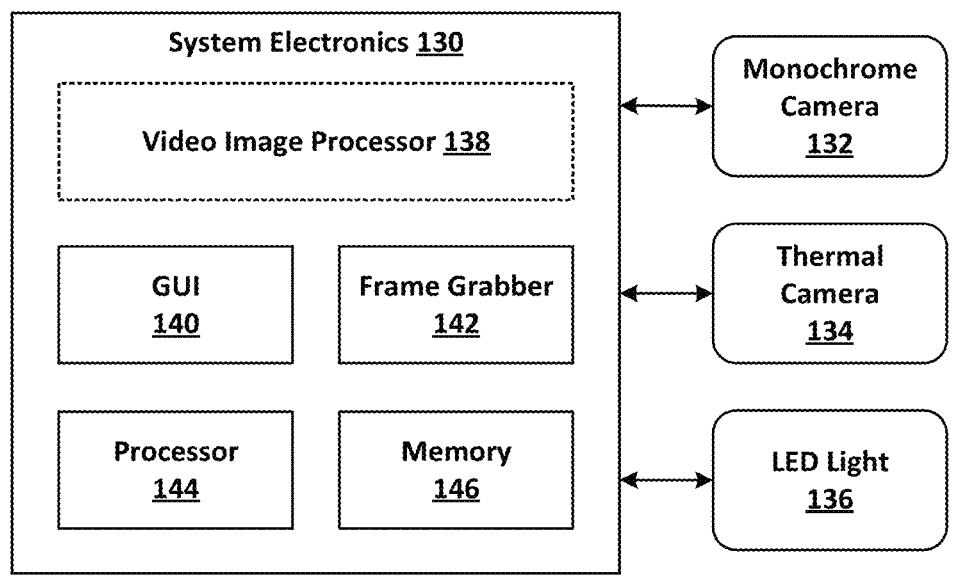
FIG. 2 is a more detailed schematic diagram of an example video monitoring device of the system of FIG. 1.

FIG. 2 is a more detailed schematic diagram of the video monitoring device 102. In this example, the video monitoring device 102 includes system electronics 130, a monochrome camera 132, a thermal camera 134, and a light emitting diode (LED) light 136.

In some embodiments, the system electronics 130 function to provide power and instructions to the monochrome camera 132, thermal camera 134, and LED light 136. In return, video images are received at the system electronics 130 from the monochrome camera 132 and thermal camera 134. The system electronics 130 function to process and analyze the images. Data produced in the analysis is communicated to one or more computing devices or computing systems. The system electronics 130 include a video image processor 138.

The monochrome camera 132 operates to capture video images of a patient on a bed. The monochrome camera 132 works in conjunction with an LED light 136 configured to illuminate the patient. The monochrome camera 132 is configured to capture light at a specific wavelength in the near infrared (NIR) spectrum. The LED light 136 is configured to emit light at the same wavelength as the monochrome camera 132. Together, the monochrome camera 132 and LED light 136 allow for continuous monitoring of a patient because it can operate in an environment lacking visible light. In some embodiments, the monochrome camera 132 has a resolution of 5 megapixels.

In some embodiments, the monochrome camera 132 is equipped with a filter to ensure that only light of the specific wavelength is recorded. In some embodiments, the monochrome camera 132 and LED light 136 operate at a wavelength within a spectral range of about 700 nanometers (nm) to 1 micrometer (µm). In some embodiments, the wavelength is selected from the spectral range of 800 nm to 900 nm. In some embodiments, monochrome camera 132 and LED light 136 operate at a wavelength within a spectral range of about 840 nm to 860 nm. In some embodiments, the wavelength is 850 nm.

Figure 5:
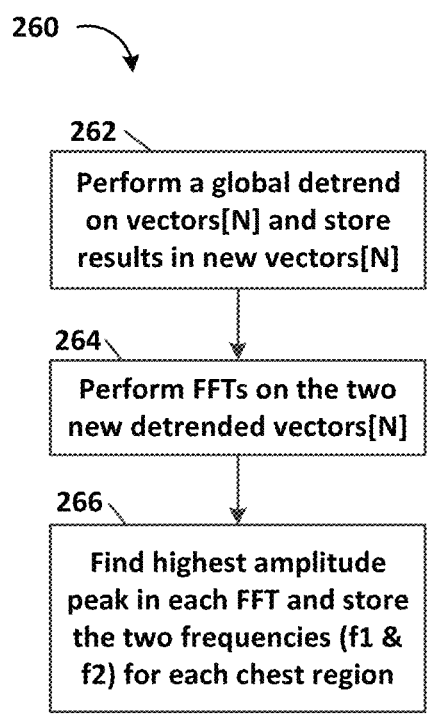
FIG. 5 is a flow chart of another possible method for performing fast Fourier transforms on data received from the video monitoring device of FIG. 1.
Figure 6:
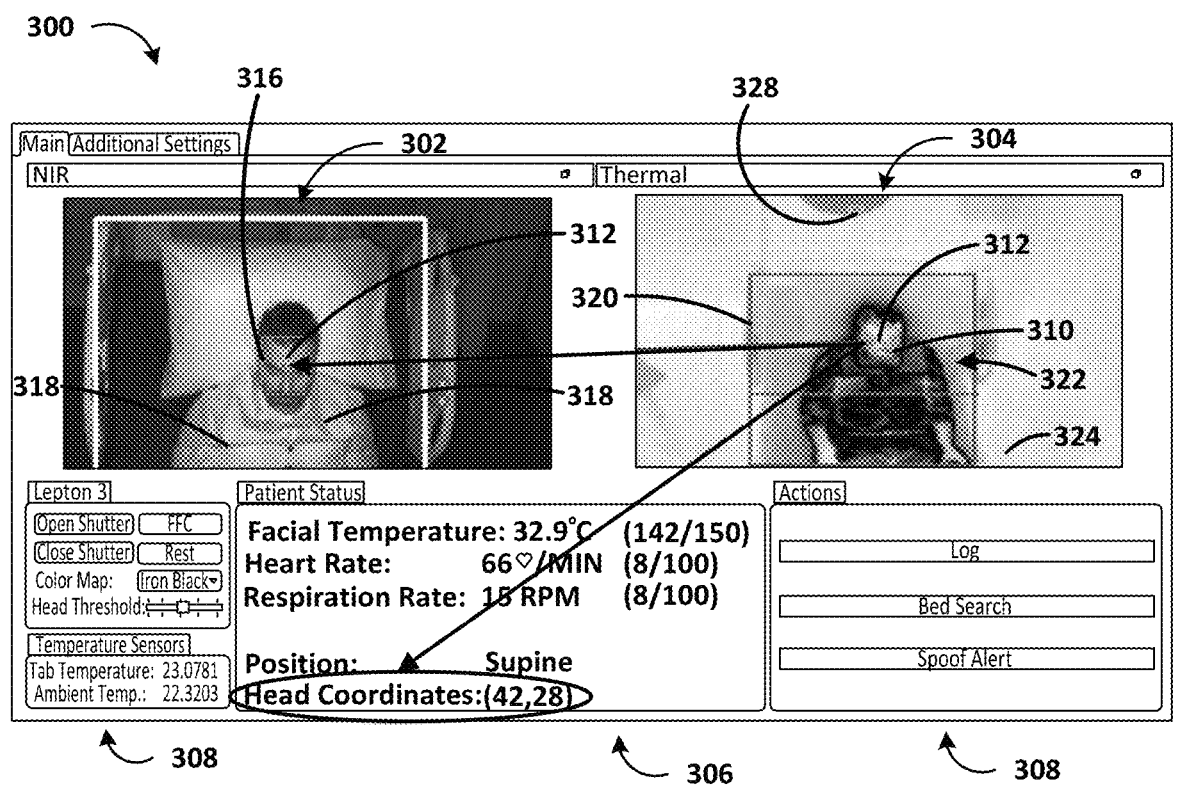
FIG. 6 illustrates a view of an example graphical user interface (GUI) usable to view data and images generated by the video monitoring device of FIG. 2.

The thermal camera 134 operates to record a surface temperature of the patient. Specifically, the thermal camera 134 is positioned such that the patient's head is in the field of view and the thermal camera 134 can obtain temperature readings to determine the location of the patient's head. The head is typically the warmest part of the body and can be seen in thermal images as a blob of warmer temperatures. Examples of this are shown in FIGS. 4-6. The temperature readings can be used both as a direct measurement of the patient's skin temperature and as a tool to locate the patient's face or head. In some embodiments, the thermal camera 134 has a resolution of 20 kilopixels. In some embodiments, the thermal camera 134 operates at a wavelength within the spectral range of 8 to 14 micrometers.

In some embodiments, the monochrome camera 132, thermal camera 134, and LED light 136 are assembled into one unit. The thermal camera 134 and monochrome camera 132 must be positioned near each other to ensure that they have a similar field of view. In some embodiments, the cameras are positioned about 7 to 8 feet from the patient. The system can be calibrated to account for any differences in measurements that occur due to different amounts of space between the cameras and the patient. Both cameras continuously record video images of the patient and communicate the video images to the system electronics 130. In some embodiments, the cameras and light are constructed within a single housing with the system electronics. In some embodiments, the system electronics 130 are housed in one unit and the cameras are housed separately.

In some embodiments, a reference tab with a temperature chip is positioned at the edge of a field of view of the thermal camera. This chip aids the system electronics 130 to correct for temperature measurement discrepancies and produce accurate temperature readings.

The video image processor 138 operates to process and analyze video images received from the cameras. One example of a method implemented by the video image processor 138 is presented in FIG. 3. In some embodiments, the video image processor 138 can compute other vital signs such as a patient's temperature and heart rate. In some embodiments, the patient's temperature is computed using an average of face pixel intensity values in the thermal image. In some embodiments, the patient's heart rate is computed using an average of face pixel intensity values in the monochrome image.

The graphical user interface (GUI) 140 operates to generate and present a display of images and data generated by the video image processor 138. One example of such a GUI 140 is shown in FIGS. 6-13. In some embodiments, the GUI 140 provides a more simplified view of the data generated by the video image processor 138. For example, the GUI 140 may only present values for various vital signs of a patient. In some embodiments, there is not a separate GUI 140 that specifically displays information generated by the video image processor 138. In such instances, the information generated is instead communicated to another computing system, such as the patient monitoring server 104, which incorporates the information into a GUI that includes other information about the patient.

The frame grabber 142 operates to capture individual, digital still frames from a video. Here, the frame grabber 142 concurrently captures frames from both the monochrome camera 132 and the thermal camera 134. In some embodiments, the frame grabber 142 captures and sends images from the cameras to the video image processor 138 at a particular frame rate within the range of 1 to 100 frames per second (fps). In some embodiments, the images are grabbed at a rate within the range of 10 to 60 fps.

The processor 144 operates to execute instructions stored in the memory 146. These instructions implement various aspects of the video monitoring device 102 to perform the methods described herein.

In some embodiments, the video image processor 138 and/or can be part of a separate, remote computing system that communicates with the cameras through wired or wireless connections. For example, the system electronics 130 could be part of the patient monitoring server 104.

FIG. 3 is a flow chart of an example method 200 of monitoring a patient's respiration rate. In some embodiments, this method 200 is performed using the system 100 of FIG. 1. The terms used in the method 200 are defined as follows:

N—Number of averages to store for calculation
N1—Number of new frames to acquire/update
vector[N]— A vector with a size of N elements
f1—Peak frequency in FFT of right chest region
f2—Peak frequency in FFT of left chest region As the cameras are continually capturing video images of the patient on the bed, a series of frames captured over a defined period of time are used in the analysis as follows. The method 200 is described in terms of analyzing one frame at a time. However, as can been seen from the flow chart, there are multiple points in the method 200 where the process returns to the starting operation 201 to repeat a subset of the operations.

At operation 202, a frame is grabbed from a thermal camera. As the thermal camera is continually capturing video images of the patient on the bed, single images need to be grabbed in order to process the images.

At operation 204, a thermal face contour is found on the frame grabbed from the thermal camera. Typically, the patient's face will be the warmest area in the camera's field of view. A "thermal blob" having a somewhat circular shape can typically be located at the patient's head. A point representing the center of the patient's face is defined within the thermal blob. In some embodiments, this point can be represented with a colored dot (e.g. red) on a display of the image frame. In some embodiments, the temperature of the patient's face is recorded in the patient's record.

At operation 206, a frame is grabbed from the monochrome camera. The monochrome frame and the thermal frame are captured contemporaneously.

At operation 208, the thermal face contour is mapped onto the monochrome frame. In some embodiments, the thermal face contour is represented by a rectangle centered on the center point of the patient's face. In some embodiments, a colored rectangle (e.g. green) is displayed to represent the face region on the monochrome frame.

At operation 210, two chest regions (right and left) are defined below the face contour. The chest regions are defined based on coordinates of the center point of the face contour. In some embodiments, the chest regions can be represented with two rectangles having a different color (e.g. blue) from the rectangle representing the face region. The chest regions are defined such that they encompass portions of the patient's body that are most likely to show movement indicative of breathing. Each chest region includes a particular number of pixels. In some embodiments, each chest region includes at least a 5×5 pixel area. The dimensions of the face contour and chest regions as well as the distances from each other could be optimized to obtain the best measurements.

In one illustrative example, the centroid of the blob of the thermal image of the face determines the centroid of the rectangular region of interest (ROI) on the face (face contour). In one case, this ROI is a rectangle having dimensions of 50 pixels wide and 65 pixels high. The two rectangular chest ROIs were set to be approximately 55×55 pixels in size. The top right corner of the left chest ROI is approximately 35 pixels directly below the bottom left corner of the facial ROT. Similarly, the top left corner of the right chest ROI is approximately 35 pixels directly below the bottom right corner of the facial ROT. This is just one example of the size and arrangement of the ROIs. Many other configurations are possible based on the equipment being used and the patient being monitored.

At operation 212, an average pixel value over each chest region is calculated. An intensity level for each and every pixel within a chest region is recorded. Generally, as the patient's chest moves closer to the camera as the patient inhales, the intensity of the pixels increases. As the patient exhales and the patient's chest moves further away from the camera, the pixel intensity decreases. The number of pixels and the range of pixel intensity values depends on the camera used to record the image. In some embodiments, the pixels have 256 different levels of intensity. All of the pixel intensity levels within the same chest region are averaged to obtain the average pixel value. The value is stored in two separate vectors[N]—one for the left chest region and one for the right chest region.

One non-limiting example of calculating the average pixel value is provided in the following equation:

$$AvePixelVal = \frac{1}{n} \times \sum_{k=1}^{n} \text{Log}(D_{k*}) * P_k$$

where $D_k$=distance ratio between centroid and perimeter; and
where $P_k$=local pixel value in a chest region and n=total number of pixels in the chest region.

This example uses a centroid gradient function: A centroid is located within the ROI. The centroid coordinates are computed as a function of the geometry of the ROI. The distance ratio between the centroid and the perimeter of the ROI is computed for every pixel, such that the pixel at the centroid is 1 and any pixel on the perimeter is 0. This is presented as $D_k$ in the equation above.

The illumination of light can be modulated by a shutter trigger of the image forming device. In such examples, all frames are divided into even $I_e$ and odd $I_o$, where even frames have illumination on and odd frames do not. This data is used to compensate for the contribution of ambient light effects in the room where the image to process ($P_k$) is then computed as a function of $f(I_e-I_o)$.

At operation 214, it is determined whether N average values are stored in the vectors[N]. The value of N is determined based on an acquisition time, which is the duration of time needed to obtain a stable reading of the patient's respiration rate. Generally, this is a predefined duration that can be adjusted by a user within a given range. For example, the user could select a fixed amount of time in the range of 15 seconds to 90 seconds. In some embodiments, the range of possible durations is 30 seconds to 60 seconds. If a sufficient number of average values have been stored in the vectors[N], the method proceeds to operation 216. If not, the method proceeds back to operation 201.

At operation 216, fast Fourier transforms (FFTs) are performed on the data from the two vectors[N] to obtain a peak frequency for each chest region (f1 and f2). Detailed examples of two possible methods of performing this operation are provided in FIG. 4. The values for f1 and f2 are stored.

At operation 218, the respiration frequency is validated. If f1 and f2 have similar values, this indicates that readings for both chest regions are similar and the patient is most likely lying on their back. For example, if f1 and f2 are within 3 rpm of each other, this indicates that frequencies are valid, and the method can proceed to the next operation. However, if f1 and f2 have a discrepancy, this could indicate that the readings for one chest region are better than the other. Mostly likely this would be due to a patient lying on their side. In that case, only the chest region having the larger FFT curve area will be used to validate the respiration frequency in order to have an adequate respiration region.

At operation 220, consistency of the respiration frequency computed in operation 218 is determined by checking the respiration frequency against previous values. For example, if it is determined that 3 out of 4 consecutive respiration frequency values are within 3 rpm of each other, the respiration frequency is considered to be consistent with previous values. If yes, the method proceeds to operation 222. If no, the method proceeds back to operation 201 and the earliest of the compared frequency values is dropped.

At operation 222, f is validated as the respiration rate. The method then continues to periodically repeat, returning to operation 201, as long as the patient is being monitored.

In the example shown, the method 200 uses thermal information from the thermal camera and monochrome information from the NIR camera to estimate the respiration rate. However, additional modalities can be used in alternative embodiments. For example, in other implementations, information from one or more of the following cameras can be used: color image camera, IR camera, and/or a depth camera (e.g., Lidar, mmWave radar, etc.). For instance, the resulting image data, such as depth, can be mapped into a special domain that coordinates to the corpus of the patient, as described further herein.

For example, a depth imaging camera can be used in place of or conjunction with the thermal camera. The depth camera captures a volumetric point cloud, and the face contour is determined as a function of minimum distance from the camera lens.

In another embodiment, the monochrome camera can be replaced by a depth imaging camera. In such an example, the average grayscale value is replaced with the Z-distance parameter from the point cloud.

FIGS. 4 and 5 include flow charts illustrating two alternative methods of performing FFTs to obtain peak frequencies. Method 240 in FIG. 4 is used by default to calculate a respiration frequency. Method 260 in FIG. 5 is used when overall baseline values of the recorded values begin to trend over time. Detrending is performed to eliminate the effects of those trends to produce a more accurate output.

As shown in FIG. 4, method 240 begins with operation 242. FFTs are performed on the raw data located in the two vectors[N]. Then, at operation 244, the area under the FFT curve for the right region and left region is calculated.

As shown in FIG. 5, method 260 begins with operation 262. A global detrend is performed on the vectors[N]. An example of this process is described with reference to FIG. 12. At operation 264, FFTs are performed on the two new detrended vectors[N]. Then, at operation 266, the highest amplitude peak in each FFT is found. The two frequencies (f1 & f2) for the right and left chest regions are stored.

FIGS. 6-13 illustrate various views of a graphical user interface (GUI) 300 usable to view images and information output by the video image processor 138. In some embodiments, the GUI 300 is the GUI 140 described in FIG. 2. The GUI 300 depicted in FIGS. 6-13 is merely exemplary and various other configurations are possible for presenting the same information.

Figure 7:
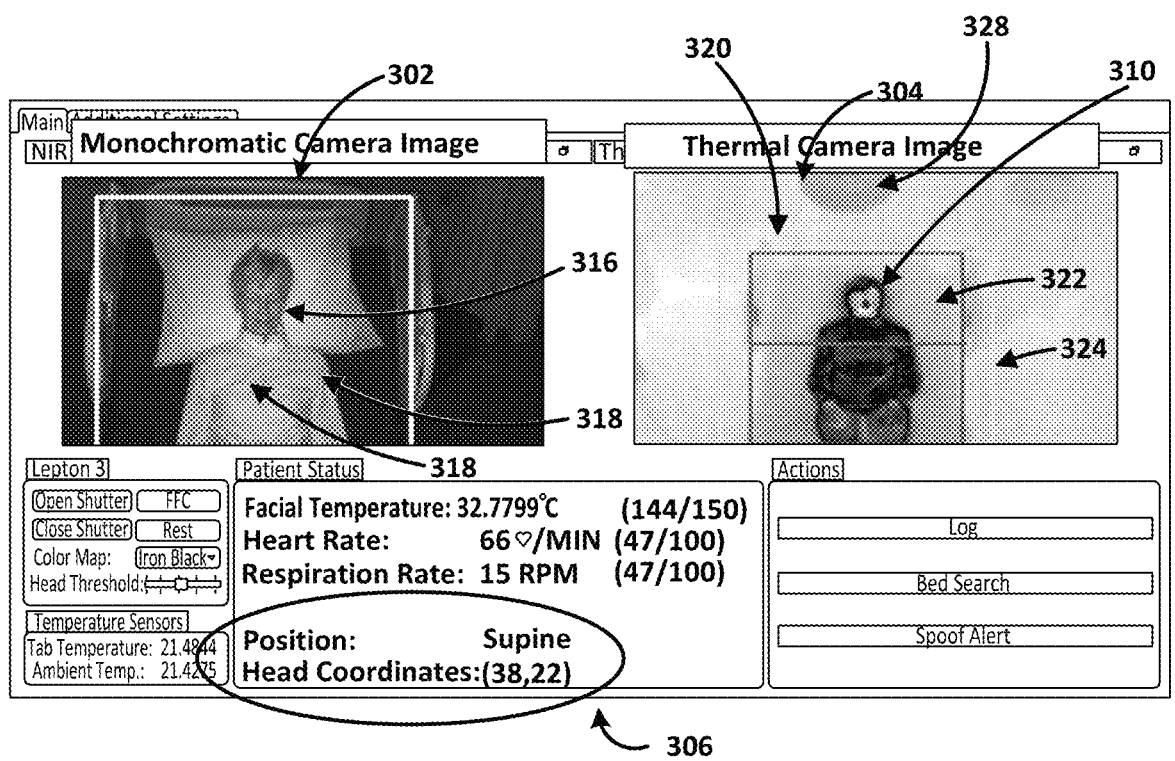
FIG. 7 illustrates an additional view of the GUI of FIG. 6.

FIG. 6 shows an example display of the GUI 300 when the video monitoring device 102 is used to monitor a male patient. A female patient is shown in the display of FIG. 7. In both views, the GUI 300 includes a display of a monochromatic camera image 302 and a thermal camera image 304. The GUI 300 also includes a patient status panel 306 configured to display information about vital signs calculated with data obtained by the video monitoring device 102. In some embodiments, the GUI 300 can include other panels 308 to provide additional information and options. In some embodiments, the thermal blob and other visual indicators are not displayed to a user on the GUI 300 and instead the display focuses only on providing the vital signs information.

In the examples of FIGS. 6-7, the vital signs data displayed in the patient status panel 306 includes facial temperature, heart rate, and respiration rate. Additionally, the patient status panel 306 includes an indication of the body position of the patient (supine) as well as head coordinates.

In this example, the patient status panel 306 includes an indication of when the particular vital sign data point was last taken. The values for the heart rate and respirate rate on the GUI are updated every 100 data points. The temperature displayed is updated every 150 data points. For example, FIG. 6 shows 66 bpm for heart rate and 15 respirations per minute on the GUI. These two values were updated 8 data points ago (at 60 frames per second that their values were updated 0.13 seconds ago). The displayed heart rate and respiration rate values will change 92 data points later (1.5 seconds later) when the fraction shows 100/100. If you were to see the GUI during a measurement, the fractions are continuously counting up from 0/100 to 100/100 and then they start over again at 0/100.

The thermal camera image 304 shows an artificially colored representation of the patient. In this example, the brightly colored areas indicate higher temperatures and the areas of lower temperatures are left dark. A particularly bright, circular spot coincides with the patient's head. This thermal face contour 310 or "thermal blob" is used to locate a point representing the center of the patient's face. This "face center" 312 point is used to determine the head coordinates of the patient. Additionally, the face center 312 is mapped onto the monochrome camera image 302. From there, a face region 316 is defined on the monochrome camera image 302 based on the location of the face center 312. In this example, the face region 316 is visualized with a rectangle. Rectangles are also used to represent the left and right chest regions 318 which are located based on a relative position from the face region 316. In some embodiments, the various points and boxes can be visually distinguished from one another with different colors.

The thermal camera image 304 can also include other visual indicators such as a bed boundary 320, a head rest region 322, bed exit boundary 324, and reference tab 328.

Figure 8:
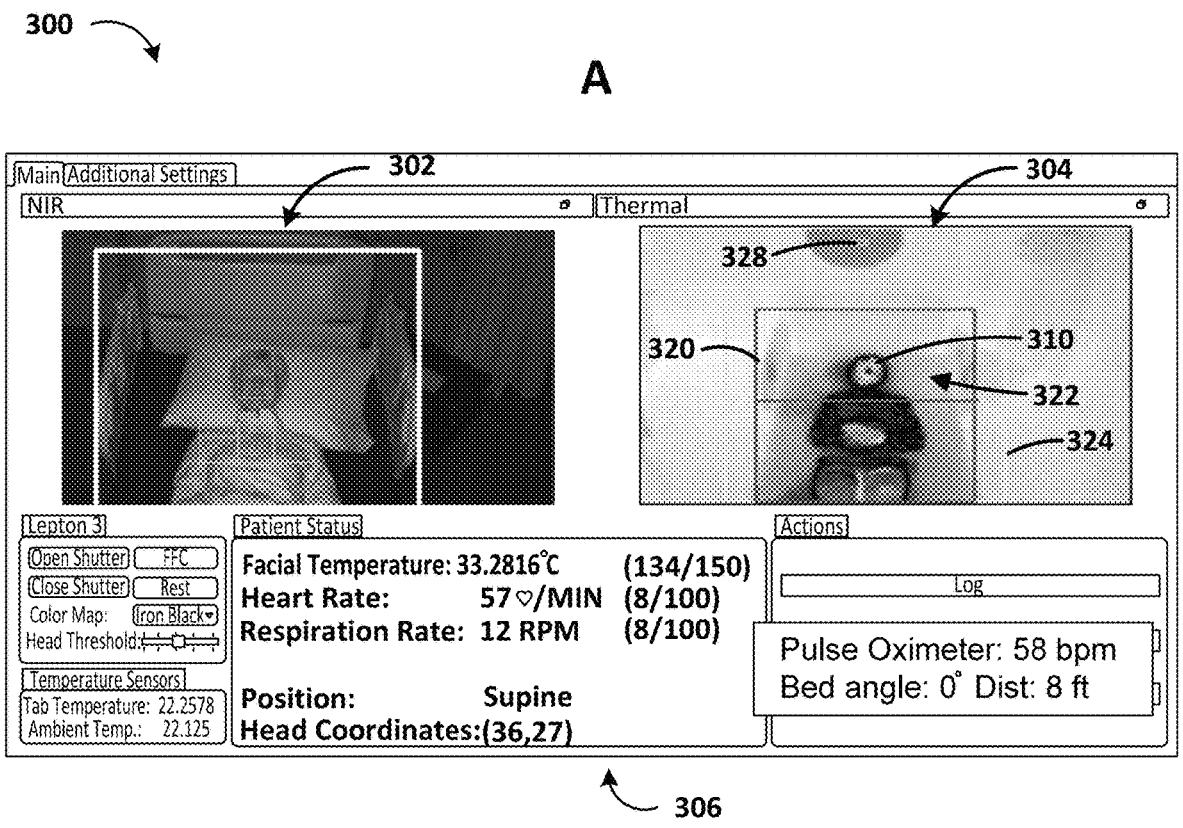
FIG. 8 illustrates an additional view of the GUI of FIG. 6.
Figure 9:
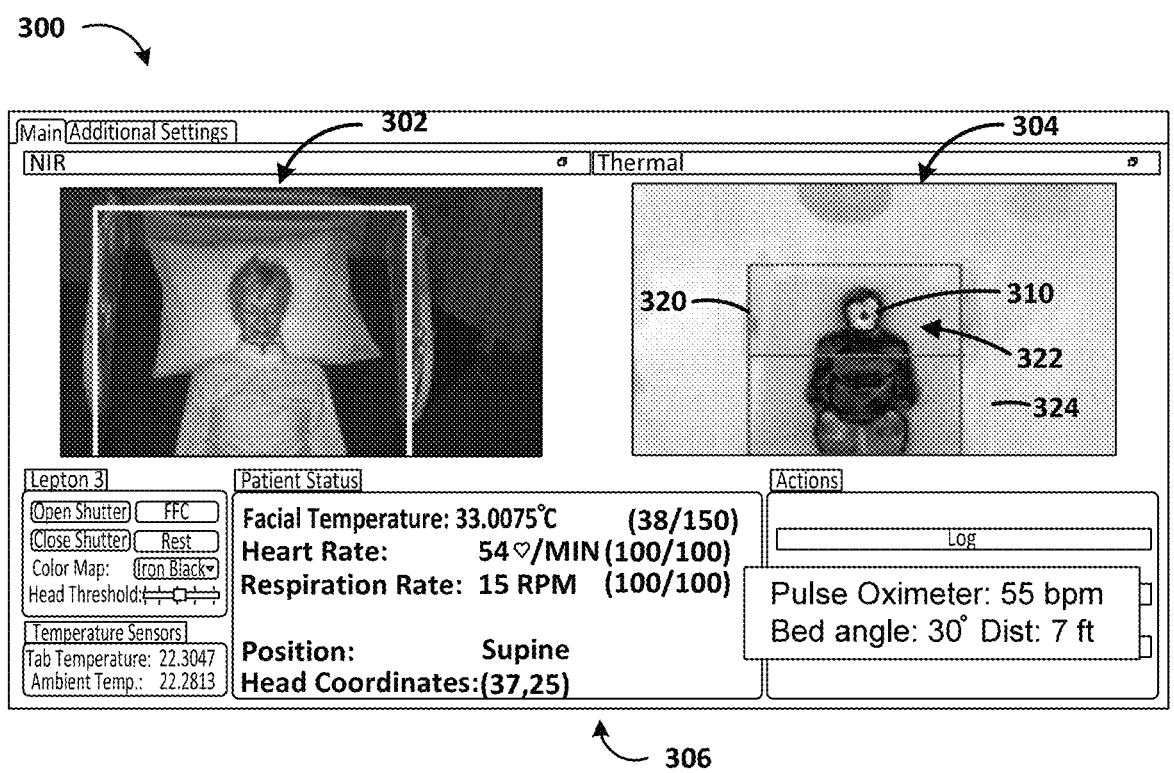
FIG. 9 illustrates an additional view of the GUI of FIG. 6.

FIGS. 8-9 shows another two views of the GUI 300. In FIG. 8, the bed is flat. In FIG. 9, the same bed is raised 30 degrees. These two figures illustrate that the system can still determine the location of the bed boundary 320, a head rest region 322, bed exit boundary 324, and thermal face contour 310 on the thermal camera image 304. In turn, the face region 316 and chest regions 318 can also be determined.

Figure 10:
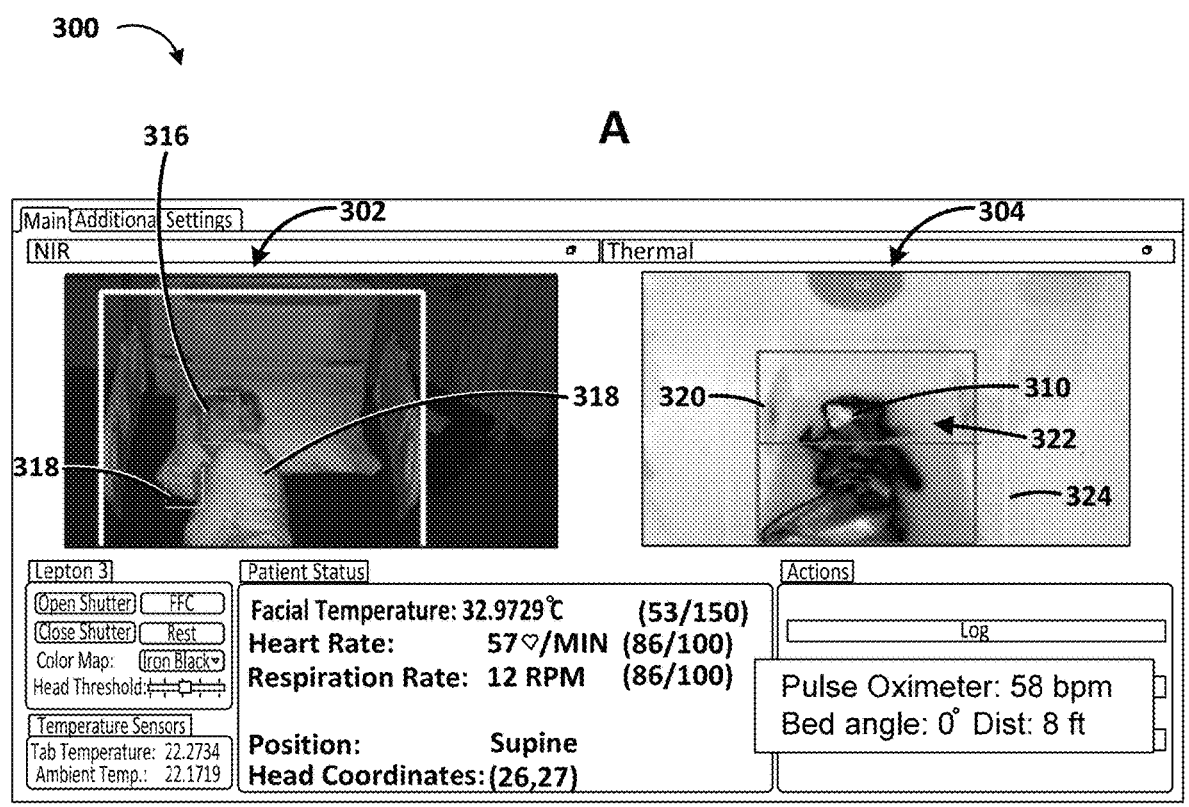
FIG. 10 illustrates an additional view of the GUI of FIG. 6.
Figure 11:
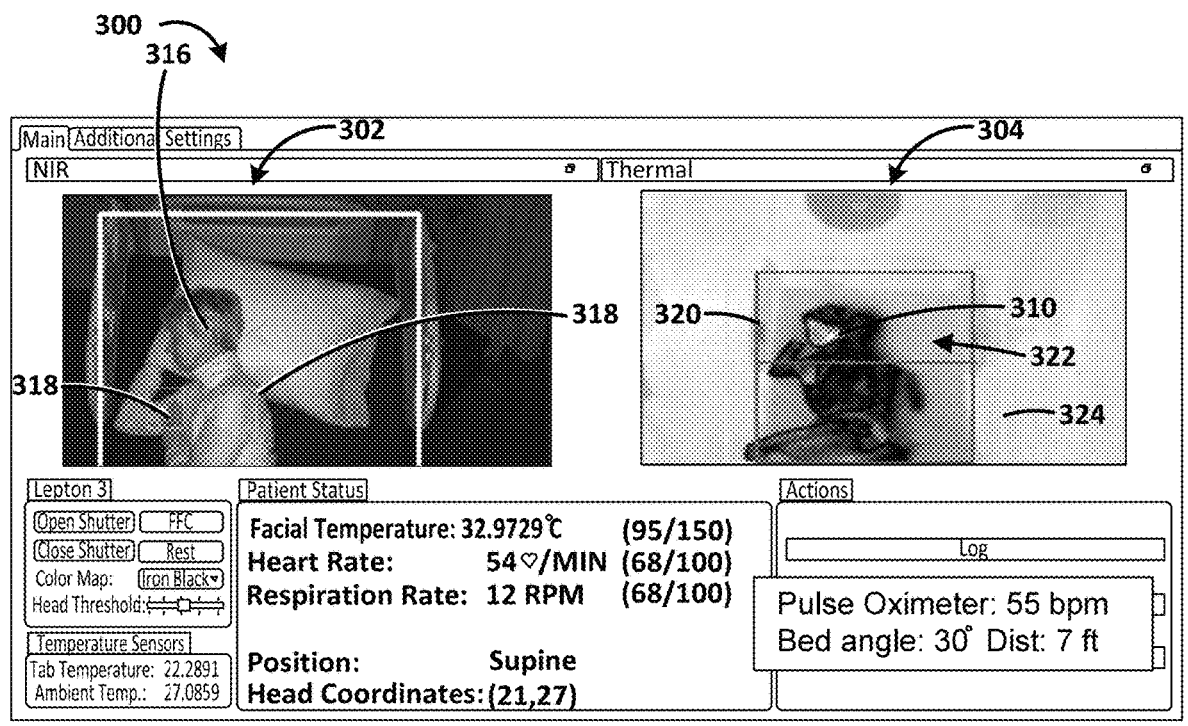
FIG. 11 illustrates an additional view of the GUI of FIG. 6.

FIGS. 10-11 show two views of the GUI where the patient is lying on her side. Again, the system is able to determine the locations of all relevant reference markers and regions. In this example, it is likely that only one chest region 318 will be used to calculate the patient's respiration rate.

Figure 12:
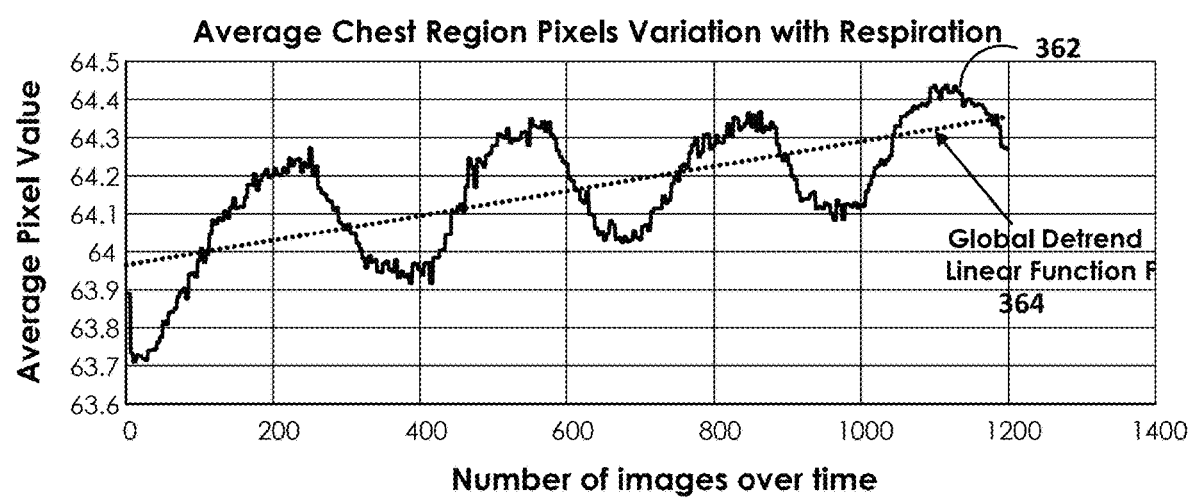
FIG. 12 presents a graph representing average chest region pixels variation with respiration.
Figure 13:
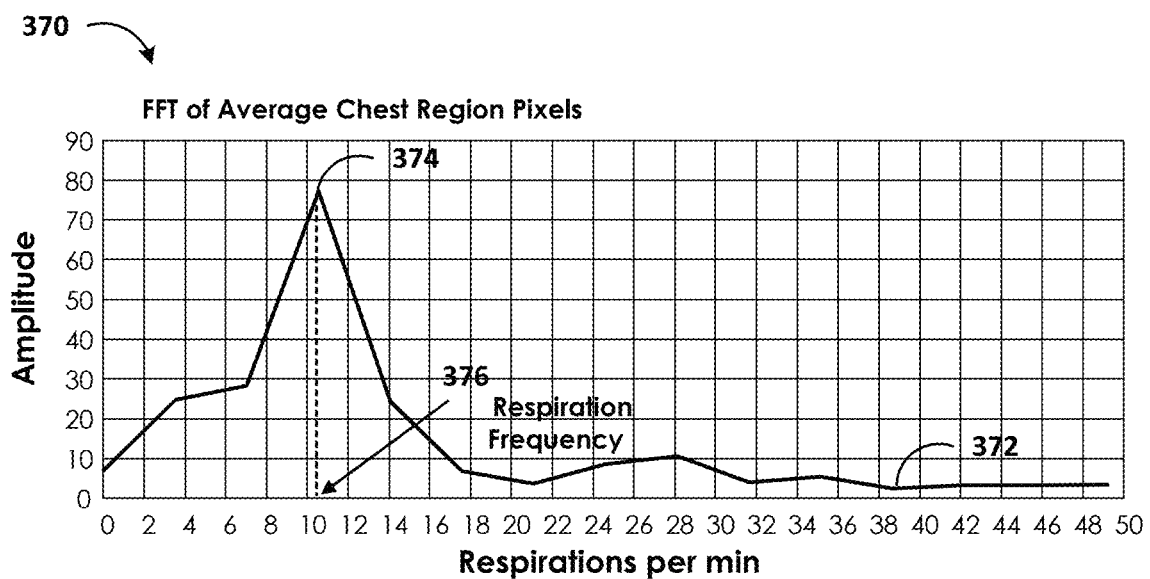
FIG. 13 present a graph of average chest region pixels after performing a fast Fourier transform on the data from FIG. 12.

FIGS. 12-13 presents graphs representing data obtained with a video monitoring system to determine a patient's respiration rate. In FIG. 12, the graph 360 shows a graph of average pixel values plotted against number of images over time. This produces a line chart 362 having regular increases and decreases in the average pixel values, which indicates respiration cycles. In this example, there is also a general upward trend (represented by the trend line 364) as more images are obtained due to signal drift. To obtain accurate respiration values, the effects of this trend are removed in a detrending process. In this example, a global detrend is performed by subtracting a linear interpolation function F(t).

FIG. 13 shows the result of the detrending in graph 370. Amplitude is plotted against respirations per min, producing a line chart 372 with one large peak. In this example, the highest amplitude peak 374 is at about 10 respirations per minute. Thus, the respiration frequency 376 is about 10 respirations per minute.

Figure 14:
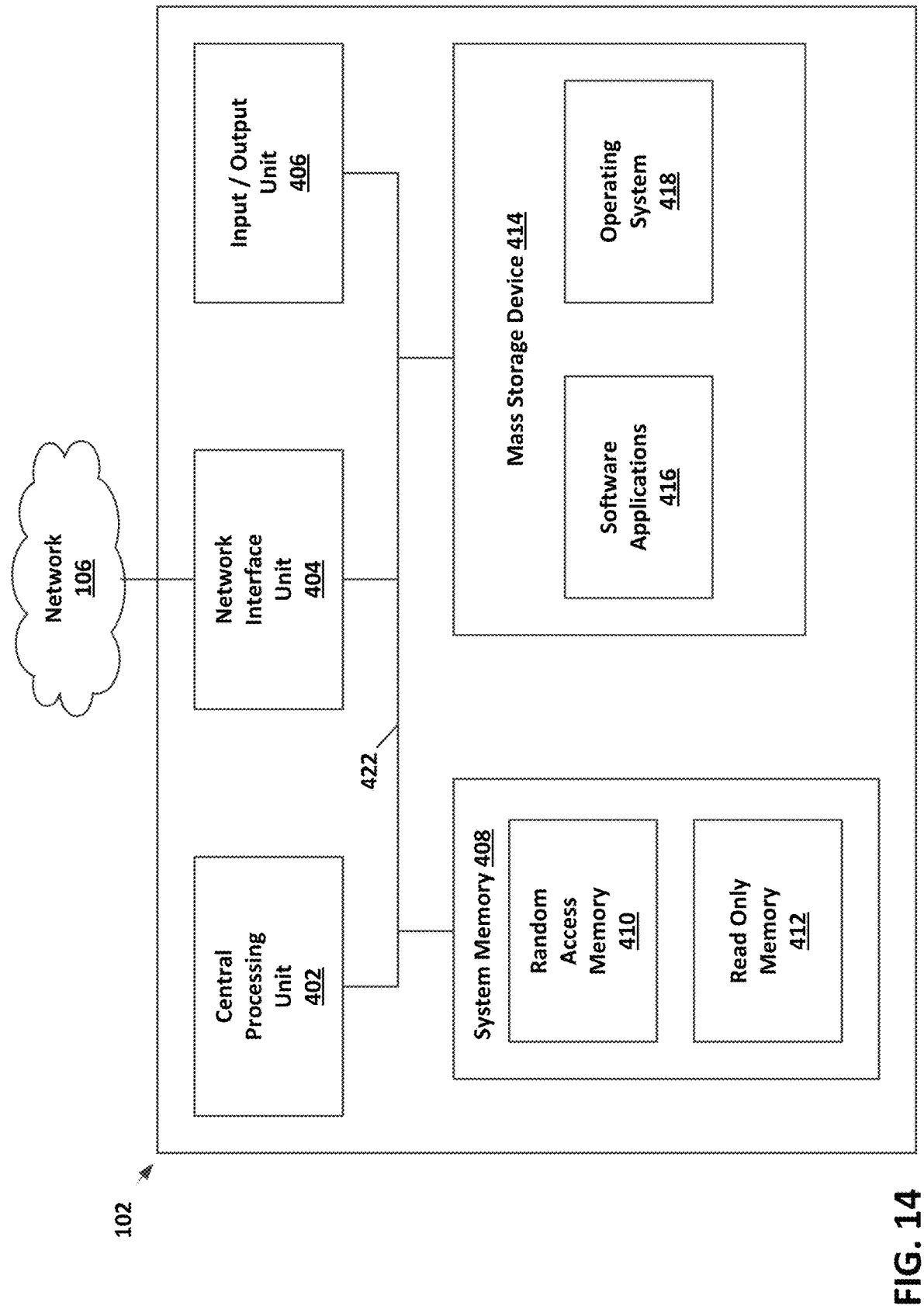
FIG. 14 is a schematic block diagram of example components of the video monitoring device of FIG. 2.

FIG. 14 is a block diagram illustrating example physical components of the video monitoring device 102. The components could also be used as part of the patient monitoring server 104 and/or other computing devices associated with the system 100.

In the example shown in FIG. 14, the video monitoring device 102 includes at least one central processing unit ("CPU") 402, a system memory 408, and a system bus 422 that couples the system memory 408 to the CPU 402. The system memory 408 includes a random access memory ("RAM") 410 and a read-only memory ("ROM") 412. A basic input/output system that contains the basic routines that help to transfer information between elements within the video monitoring device 102, such as during startup, is stored in the ROM 412. The video monitoring device 102 further includes a mass storage device 414. The mass storage device 414 is able to store software instructions and data usable to implement various aspects of the patient monitoring system 100.

The mass storage device 414 is connected to the CPU 402 through a mass storage controller (not shown) connected to the system bus 422. The mass storage device 414 and its associated computer-readable storage media provide non-volatile, non-transitory data storage for the video monitoring device 102. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the video monitoring device 102.

According to various embodiments, the video monitoring device 102 can operate in a networked environment using logical connections to remote network devices through a network 106, such as a wireless network, the Internet, or another type of network. The video monitoring device 102 may connect to the network 106 through a network interface unit 404 connected to the system bus 422. It should be appreciated that the network interface unit 404 may also be utilized to connect to other types of networks and remote computing systems. The video monitoring device 102 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the video monitoring device 102 can store software instructions and data. The software instructions include an operating system 418 suitable for controlling the operation of the video monitoring device 102. The mass storage device 414 and/or the RAM 410 also store software instructions, that when executed by the CPU 402, cause the video monitoring device 102 to provide the functionality discussed in this document. For example, the mass storage device 414 and/or the RAM 410 can store software instructions that, when executed by the CPU 402, cause the video monitoring device 102 to process video images to compute patient vital signs.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method of monitoring a respiration rate of a patient, the method comprising:
    obtaining videos of the patient on a bed recorded contemporaneously with a thermal camera and a monochrome camera, wherein the thermal camera and the monochrome camera are part of a video system positioned over the bed occupied by the patient;
    analyzing, with a video image processing unit, the videos one frame at a time by performing the following operations:
        grabbing a frame from the video recorded by the thermal camera and grabbing a frame from the video contemporaneously recorded by the monochrome camera;
        finding a thermal face contour of the patient on the frame from the thermal camera;
        mapping the thermal face contour onto the frame from the monochrome camera;
        defining a left chest region and a right chest region positioned adjacent to the thermal face contour;
        calculating an average left pixel intensity value within the left chest region and an average right pixel intensity value within the right chest region;
        storing a left vector associated with the average left pixel value for the left chest region and a right vector associated with the average right pixel value for the right chest region;
        performing fast Fourier transforms on the left vector and the right vector to compute a respiration frequency; and
        validating the respiration frequency as the respiration rate.

2. The method of claim 1, further comprising repeating the analyzing at regular time intervals to obtain a real-time respiration rate for the patient.

3. The method of claim 2, wherein the analyzing is performed at a frequency computed as a function of an expected respiration rate, wherein the frequency is selected in the range of 10 fps to 60 fps.

4. The method of claim 1, wherein the thermal face contour is defined as a rectangular region, the left chest region is a rectangular region positioned spaced apart from the thermal face contour such that a center of the left chest region is below a bottom left corner of the thermal face contour, and the right chest region is a rectangular region positioned spaced apart from the thermal face contour such that a center of the right chest region is below a bottom right corner of the thermal face contour.

5. The method of claim 1, wherein an average pixel value is calculated using the following equation:

$$AvePixelVal = \frac{1}{n} \times \sum_{k=1}^{n} \text{Log}(D_{k*}) * P_k$$

where $D_k$=distance ratio between centroid and perimeter; and where $P_k$=local pixel value in a chest region and n=total number of pixels in the chest region.

6. The method of claim 1, wherein the monochrome camera is configured to detect near infrared (NIR) having a wavelength within a spectral range of about 700 nanometers to 1 micrometer, and a light-emitting diode (LED) is configured to continuously emit light having a similar wavelength.

7. The method of claim 1, wherein the thermal camera is configured to detect long-wavelength infrared (LWIR) light having a wavelength within a spectral range of about 6 to 17 micrometers.

8. The method of claim 1, wherein performing FFTs comprises:
    performing FFTs on the data stored in the two vectors,
    producing a curve for each set of data, and
    calculating an area under the curve for each set of data.

9. The method of claim 1, wherein performing FFTs comprises:
    performing global detrend on each of the two vectors,
    storing results of the detrend in new vectors,
    performing FFTs on the new detrended vectors,
    finding a highest amplitude peak in each FFT, and
    storing a frequency for the right chest region and a frequency for the left chest region.

10. The method of claim 1, wherein validating the respiration frequency as the respiration rate comprises:
    determining whether the frequency for the right chest region is within 3 rpm of the frequency for the left chest region, and, if not, use a chest region having a larger FFT curve area to select an adequate respiration region for validating a respiration frequency;
    when 3 out of 4 consecutive f values are within 3 rpm, validating f as the respiration rate; and
    when 2 or fewer out of 4 consecutive f values are within 3 rpm, repeating the analyzing of the video.

11. The method of claim 1, further comprising communicating the respiration rate to a caregiver computing device in real-time.

12. A patient monitoring system comprising:
    a video system including a thermal camera and a monochrome camera positioned over a bed occupied by a patient;
    a processor in communication with the video system; and a memory comprising instructions that, when executed, cause the processor to perform a series of operations comprising:
  (a) grabbing a frame from video recorded with the thermal camera and grabbing a frame from the video recorded with the monochrome camera at the same time as the video recorded with the thermal camera;
  (b) finding a thermal face contour of a patient on the frame from the thermal camera;
  (c) mapping the thermal face contour onto the frame from the monochrome camera;
  (d) defining a center point of a head and recording coordinates for the center point; and
  (e) computing a physical parameter of the patient using the thermal face contour and the center point of the head.

13. The patient monitoring system of claim 12,
wherein the thermal camera is configured to detect long-wavelength infrared (LWIR) light;
wherein the monochrome camera is configured to detect near-infrared (NIR) light; and
wherein the video system further includes a light-emitting diode (LED) light configured to emit the NIR light.

14. The patient monitoring system of claim 13, wherein the monochrome camera operates at a wavelength within a spectral range of about 700 nanometers to 1 micrometer.

15. The patient monitoring system of claim 14, wherein the monochrome camera operates at an 850 nanometer wavelength.

16. The patient monitoring system of claim 14, wherein the LED light is configured to provide continuous illumination at a wavelength within a spectral range of about 700 nanometers to 1 micrometer.

17. The patient monitoring system of claim 13, wherein the thermal camera operates at a wavelength within a spectrum of 8 to 14 micrometers (µm).

18. A patient monitoring system comprising:
a processor; and
a memory comprising instructions that, when executed, cause the processor to perform a series of operations comprising:
  (a) grabbing a frame from video recorded with a first camera and grabbing a frame from the video recorded with a second camera at the same time as the video recorded with the first camera, wherein the first camera and the second camera are part of a video system positioned over a bed occupied by a patient;
  (b) finding a face contour of the patient on the frame from the first camera;
  (c) mapping the face contour onto the frame from the second camera;
  (d) defining a center point of a head and recording coordinates for the center point; and
  (e) computing a physical parameter of the patient using the face contour and the center point of the head;
  (f) wherein the first camera is a depth camera defining a volumetric point cloud; and
  (g) wherein the second camera is a thermal camera or a monochrome camera.

19. The patient monitoring system of claim 18, wherein, when the second camera is the thermal camera, the face contour is determined as a function of minimum distance from a lens, and wherein, when the second camera is the monochrome camera, the face contour is determined using a Z distance parameter from the volumetric point cloud.

* * * * *